(12) United States Patent
Setiabudi et al.

(10) Patent No.: US 7,177,676 B2
(45) Date of Patent: Feb. 13, 2007

(54) SYSTEM AND METHOD FOR ANALYZING BIOFEEDBACK INFORMATION FOR PERFORMANCE OF AN INDIVIDUAL IN A GROUP

(75) Inventors: J. Dwidjaja Setiabudi, Kudus (ID); Adisusanto, Kudus (ID); Max Arief Pramono, Kudus (ID); Damar Suryawan, Kudus (ID); Jojok Sadikin, Kudus (ID); Min Nursandi, Kudus (ID); Eva Christin, Kudus (ID)

(73) Assignee: Pt. Hartono Istana Teknologi, Kudus (ID)

(*) Notice: Subject to any disclaimer, the term of this patent is extended or adjusted under 35 U.S.C. 154(b) by 230 days.

(21) Appl. No.: 10/759,119

(22) Filed: Jan. 20, 2004

(65) Prior Publication Data

US 2005/0159672 A1 Jul. 21, 2005

(51) Int. Cl.
*A61B 5/04* (2006.01)
(52) U.S. Cl. .................... 600/545; 600/544
(58) Field of Classification Search ................ 600/545, 600/544, 301
See application file for complete search history.

(56) References Cited

U.S. PATENT DOCUMENTS

| | | | |
|---|---|---|---|
| 6,097,981 A * | 8/2000 | Freer ........................ 600/545 |
| 6,102,846 A | 8/2000 | Patton et al. ................. 600/26 |
| 6,175,762 B1 | 1/2001 | Kirkup et al. ............... 600/544 |
| 6,234,965 B1 | 5/2001 | Miller et al. ................ 600/300 |
| 6,261,236 B1 | 7/2001 | Grimblatov .................. 600/500 |
| 6,434,419 B1 * | 8/2002 | Gevins et al. ............... 600/544 |
| 6,527,700 B1 * | 3/2003 | Manico et al. ................ 600/26 |

* cited by examiner

Primary Examiner—Max F. Hindenburg
Assistant Examiner—Anuradha Roy
(74) Attorney, Agent, or Firm—Birch, Stewart, Kolasch & Birch, LLP

(57) ABSTRACT

A biofeedback system and method for analyzing the performance of an individual and group. The system employs a plurality of transducers for transmitting biofeedback and brain wave information as well as other biological information such as heart rate, pulse, body temperature, etc. This information is individually analyzed relative to the following neurotechnology (Neutech) formula:

$$f_{bhwd} \sim 2^{(3-N)} \times f\theta$$

Where:

$$N = \sim 0 \sim 1 \sim 2 \sim 3 \sim 4 \sim 5 \sim$$

In one embodiment, a plurality of transmitters are provided for receiving biofeedback and brain waves and other information unique to the specific user. This data is then collected and transmitted and the data processed with subsequent demonstration of process data in the form of biofeedback information.

7 Claims, 2 Drawing Sheets

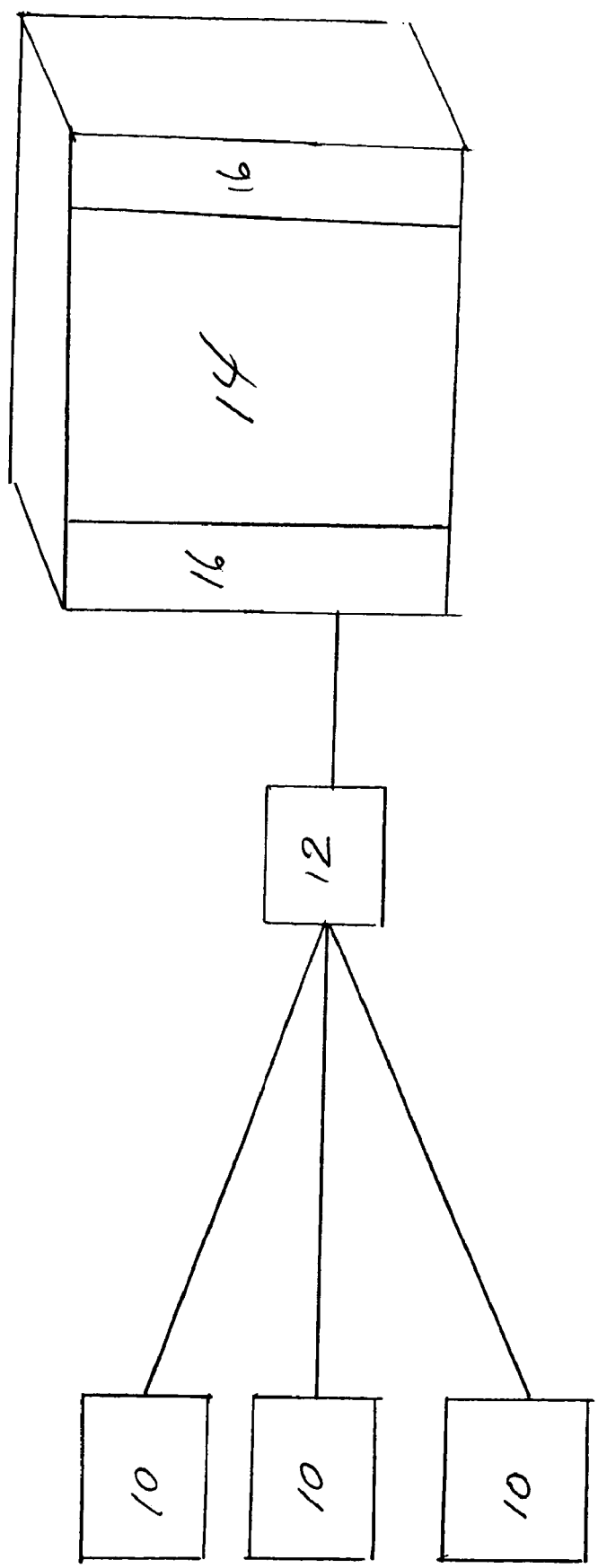

SYSTEM AND METHOD FOR ANALYZING BIOFEEDBACK INFORMATION FOR PERFORMANCE OF AN INDIVIDUAL IN A GROUP

CROSS-REFERENCE TO RELATED APPLICATIONS

This is the first application filed for the present invention.

FIELD OF THE INVENTION

The present invention relates to a system and method for analyzing biofeedback information to assess the performance of an individual in a group and more particularly, the present invention relates to a system and method where biofeedback information can be obtained to translate into constructive performance information for an individual.

In the prior art, and in particular, U.S. Pat. No. 6,102,846, issued Aug. 15, 2000 to Patton et al., discusses the system and method for managing a psychological state of an individual using images to achieve this goal. In the disclosure the system facilitates stress management by viewing images based on those selected from an individual's personal profile. The profile is created by the individual viewing a number of images and those with the best possible biofeedback are selected and this information or data is used to co-act with a biofeedback system in order to assist the individual in stress management.

A further variation on the biofeedback systems and methods of the prior art is illustrated by Grimblatov, in U.S. Pat. No. 6,261,236, issued Jul. 17, 2001. The disclosure of this reference sets forth a method and apparatus capable of coordinating the physical action of systolic and diastolic cycles of an individual's circulatory system. It has been found that this has efficacy in synchronizing treatment action with homoeostatic rhythms of the body which facilitates more predictability in the treatment effect of the medication.

In U.S. Pat. No. 6,234,965, issued to Miller et al., May 22, 2001, a method and apparatus for improving biochemical based therapy is set forth.

In the reference, a computer system is employed for enhancing biochemical therapy among other forms of therapy in a human. This system is primarily used to determine the efficacy of a prescribed compound.

Although the prior art has generally related to useful systems and devices for biofeedback, no such system has been employed to determine the performance characteristics of a single individual within a group. The present invention is directed to such methodology.

The method used is a method based on neurotechnology (Neutech) and includes the formula:

$$fBHWD = 2^{(3-N)} f(\theta) Hz$$

BACKGROUND OF THE INVENTION

In a meeting/lecture/workshop, there are active and passive participants. Generally there are a few levels between enthusiastic participants and those who are apathetic. In reality, the participants' biofeedback and brain wave data is representative of their characteristics. Everyone will automatically be motivated for his own betterment, to generate a Human-Awareness-Quotient (H-A-Q). Further, the degree of willingness of the participants will be determined on an individual basis by analysis of the data. Through this display system, the data can be used to establish a reliable, focused group of individuals for a specific task. The display is executed from the beginning for a plan until the real end result. From the outset, every step of seven steps, Plan-Do-Check-Action-Sharing-Release-$\theta$ wave state (P-D-C-A-S-R-$\theta$) may be recorded in harmony. Through this display system, anyone can transparently learn to understand from those who do not understand, and learn to help others who do not understand. "Sharing" would occur if a participant understands, and "asking" if they do not know. In the system, nothing can be concealed because biofeedback, brain wave and other data for each participant is displayed clearly. On the other hand, the participant who is shackled with their vision-mission will be trained to find the best solution, so he himself is not buried by their vision-mission (shackled in a "dream"-nega-theta-wave)

SUMMARY OF THE INVENTION

One object of the present invention is to provide an improved biofeedback system and method for obtaining the maximum amount of information from an individual to enhance his or her performance either standing alone or within the framework of a group.

A further object of one embodiment of the present invention is to provide a system for analyzing biofeedback information for performance and motivation level of an individual in a group, comprising:
  a plurality of transmitters for receiving and transmitting biofeedback and brain waves;
  a processor means in electrical communication with the plurality of transmitters for processing transmitted data; and
  demonstration means for demonstrating processed data.

A still further object of the present invention is to provide a method for collecting biofeedback and brain waves for performance and motivation level of a individual in a group, comprising:
  providing a plurality of transmitters for receiving and transmitting biofeedback and brain waves;
  positioning a transmitter on a user;
  collecting transmitted data from each user;
  processing the transmitted data; and
  demonstrating processed data in the form of biofeedback information.

Having thus generally described the invention, reference will now be made to the accompanying drawings.

BRIEF DESCRIPTION OF THE DRAWINGS

Further features and advantages of the present invention will become apparent from the following detailed description, taken in combination with the appended drawings, in which:

FIG. 2 is a schematic illustration of a schematic illustration of one embodiment of the apparatus according to the present invention.

It will be noted that throughout the appended drawings, like features are identified by like reference numerals.

DETAILED DESCRIPTION OF THE PREFERRED EMBODIMENT PREFACE

Figure 1:
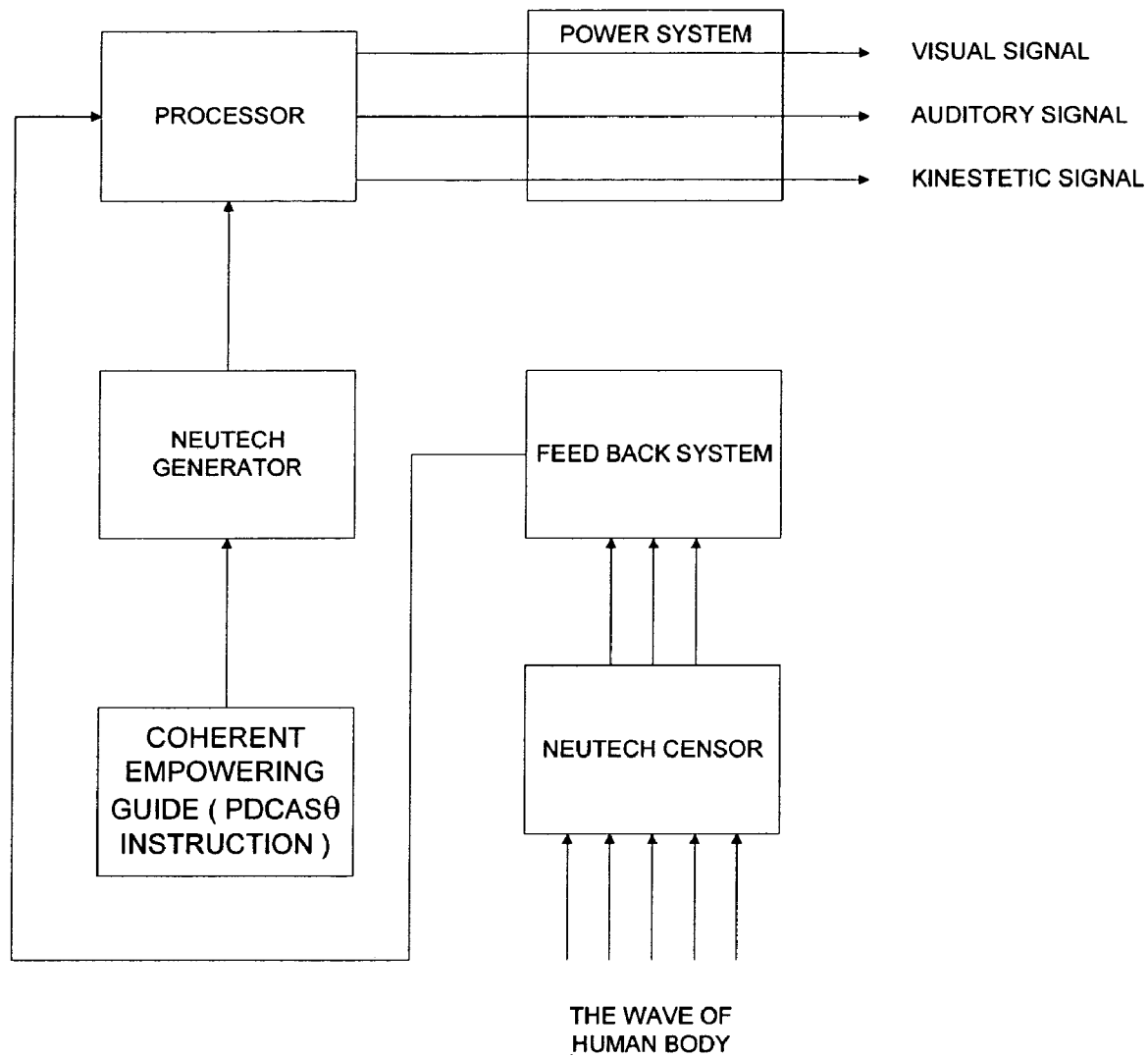
FIG. 1 is a schematic illustration of one process according to the present invention.

FIG. 1 schematically illustrates the overall process. Generally speaking, real-time data display systems are particularly useful in assessing information immediately. The system of the present invention integrates psychology, neurophysiology, electronics and biofeedback principles for assessing the motivation and increasing the performance of an individual.

The merit of biofeedback has been well documented and the applicability of this information to the present invention is to assess an individual's motivation and potential for performance.

The system employs the following formula:

$$f_{bhwd} \sim 2^{(3-N)} \times f\theta$$

Where:

$$N = \sim 0 \sim 1 \sim 2 \sim 3 \sim 4 \sim 5 \sim$$

for determining a biological health wave for an individual. The value of the wave is compared with before and after values in the domain number (N). For example for N≡3, if the before value is 5 Hz and the after value is 4.5 Hz indicating a decrease representing a move to a more creative-mind, the values can be used to determine the motivation and performance level of an individual.

Table 1, set forth herein below provides examples of the data wave frequency, where N is the number of general neurotechnology for biowave energy domain in our body area (1, 2, 3, 4, 5, . . . ), such as brain, heart, lungs, etc.

Referring now to FIG. 2, shown is a schematic illustration of the apparatus in accordance with one embodiment of the present invention. In this embodiment, the transmitters are represented by numeral 10 with the information being carried from the transmitters 10 to processor 12 and subsequently on to the demonstration device, shown in the example to be a screen 14. The device 14 may also include audio speakers 16. The processor effects a comparison of the pre-transmitted and post transmitted data or N values. The results are displayed (feedback) to the individual to elicit a physical and/or emotional change.

The embodiment (s) of the invention described above is(are) intended to be exemplary only. The scope of the invention is therefore intended to be limited solely by the scope of the appended claims.

We claim:

1. A method for collecting biofeedback and brain waves for the performance and motivation levels of an individual in a group, comprising:
    providing a plurality of transmitters for receiving and transmitting biofeedback and brain waves;
    positioning a transmitter on a user;
    collecting transmitted data from each user;
    processing said transmitted data relative to a predetermined value in accordance with the Neutech formula:

$$fBHWD = 2^{(3-N)} f(\theta); \text{ and}$$

demonstrating processed data in the form of biofeedback information.

2. The method as set forth in claim 1, wherein said processed data is simultaneously collected from each said user and displayed.

3. The method as set forth in claim 1, wherein processing includes comparing pre-transmitted data with post transmitted data.

4. The method as set forth in claim 1, wherein said biofeedback information comprises visual information.

5. The method as set forth in claim 1, wherein said biofeedback information comprises audio information.

6. The method as set forth in claim 1, wherein said biofeedback information comprises kinesthetic information.

7. The method as set forth in claim 3, wherein compared processed data is displayed to said individual to effect a physical and/or emotional change.

* * * * *